(12) United States Patent
Raj et al.

(10) Patent No.: US 9,638,704 B2
(45) Date of Patent: May 2, 2017

(54) ASSAY DEVICE

(75) Inventors: Balbir Raj, Putnoe Bedford (GB); Saji Eapen, Cambridgeshire (GB); Ian Scrimgeour, Oakley (GB)

(73) Assignee: SPD SWISS PRECISION DIAGNOSTICS GMBH, Geneva (CH)

( * ) Notice: Subject to any disclaimer, the term of this patent is extended or adjusted under 35 U.S.C. 154(b) by 40 days.

(21) Appl. No.: 13/988,953

(22) PCT Filed: Nov. 24, 2011

(86) PCT No.: PCT/EP2011/070985
§ 371 (c)(1),
(2), (4) Date: Aug. 2, 2013

(87) PCT Pub. No.: WO2012/069610
PCT Pub. Date: May 31, 2012

(65) Prior Publication Data
US 2013/0309760 A1  Nov. 21, 2013

(30) Foreign Application Priority Data

Nov. 24, 2010 (GB) .................................. 1019916.4
Sep. 9, 2011 (GB) .................................. 1115613.0

(51) Int. Cl.
*G01N 33/76* (2006.01)
*G01N 33/543* (2006.01)
*G01N 33/558* (2006.01)

(52) U.S. Cl.
CPC ....... *G01N 33/76* (2013.01); *G01N 33/54366* (2013.01); *G01N 33/558* (2013.01)

(58) Field of Classification Search
CPC ........ G01N 33/76; G01N 33/74; G01N 33/50;
G01N 33/48; G01N 33/00; G01N 33/53;
G01N 33/543; G01N 33/54366; G01N
33/558; G01N 33/68; G01N 33/536;
G01N 33/537; G01N 33/538; G01N
33/544; G01N 33/549; G01N 33/5436;
G01N 33/54386; G01N 3/00; B01L 3/00;
B01L 3/5023; B01L 3/5027; B01L 3/502;
B01L 3/50
See application file for complete search history.

(56) References Cited

U.S. PATENT DOCUMENTS 5,271,895 A * 12/1993 McCroskey et al. ......... 422/408
5,384,264 A    1/1995 Chen et al.
(Continued)

FOREIGN PATENT DOCUMENTS

CN        201083738 Y    7/2008
EP          291194 A1   11/1988
(Continued)

OTHER PUBLICATIONS

International Search Report and Written Opinion for PCT/EP2011/070985 mailed Feb. 24, 2012.
(Continued)

*Primary Examiner* — Lore Jarrett
(74) *Attorney, Agent, or Firm* — David P. Halstead; Erik Huestis; Foley Hoag LLP

(57) ABSTRACT

The present invention relates generally to an assay device with improved tolerance to mishandling and/or use by the user. More particularly, the invention relates to an assay device with reduced susceptibility to flooding.

20 Claims, 4 Drawing Sheets

(56) References Cited

U.S. PATENT DOCUMENTS

| | | | |
|---|---|---|---|
| 5,415,994 | A | 5/1995 | Imrich et al. |
| 5,770,460 | A | 6/1998 | Pawlak et al. |
| 5,945,345 | A | 8/1999 | Blatt et al. |
| 6,027,943 | A | 2/2000 | Kang et al. |
| 6,046,057 | A | 4/2000 | Nazareth et al. |
| 6,277,650 | B1 | 8/2001 | Nazareth et al. |
| 2006/0008847 | A1* | 1/2006 | Ramel et al. .................. 435/7.1 |
| 2007/0148049 | A1 | 6/2007 | Esfandiari |
| 2009/0253119 | A1* | 10/2009 | Zhou et al. ....................... 435/5 |

FOREIGN PATENT DOCUMENTS

| | | |
|---|---|---|
| WO | WO-0007016 A1 | 2/2000 |
| WO | WO-2005029073 A2 | 3/2005 |

OTHER PUBLICATIONS

Combined EP Search Report and Examination Report for GB1019916.4 mailed Feb. 28, 2011.

\* cited by examiner

ASSAY DEVICE

The present invention relates generally to an assay device with improved tolerance to mishandling and/or improper use by the user. More particularly, the invention relates to an assay device with reduced susceptibility to flooding.

Various diagnostic products are known which analyse a fluid sample, such as urine or blood, to determine the presence or amount of one or more analytes. These may be small, handheld devices, which are used by applying the biological sample to an absorbent component; the devices are configured to subsequently convey the fluid along a flow path to an internal assay test zone without needing any significant gravitational encouragement, e.g. by capillary action, or user-applied pressure, where a reaction or binding event takes place to afford the assay result.

An example of a device of this nature is the lateral flow type assay device described in EP 0,291,194. This document discloses an immunoassay device comprising a type of sample application region known as a wick, which overlaps and is fluidically connected to a porous carrier containing a reagent zone bearing a mobilisable labelled specific binding reagent for an analyte. Downstream, an unlabelled specific binding reagent for the analyte is immobilised in a test zone or analyte detection zone. The user performs the single step of applying liquid sample to the wick, and the sample is subsequently conveyed along the flow path by capillary action. The device is designed to enable the controlled release of the mobilisable labelled reagent by the sample. Any analyte in the sample will then interact with the released labelled specific binding reagent to form a labelled complex, which is carried to the test zone where it forms a "sandwich" complex with the immobilised unlabelled binding reagent. The label, which may be a coloured particle, thereby becomes concentrated and observable in the test zone to indicate the presence and/or amount of analyte in the sample.

This type of assay is reliant to an extent upon the correct quantity of sample being applied by the user, upon the appropriate location and manner of sample application, and upon the correct handling of the assay device by the user. The device is capable of taking up more than the desired volume of sample, and if too much sample is applied, the assay may not run correctly. For instance, the flow rate of the sample along the flow path of the assay may be too fast, with possible consequences including analyte and mobilisable reagents being carried too quickly past the relevant zones and there being insufficient time for various binding reactions to occur; or the mobilisable labelled binding reagent may be washed away before substantial binding can occur. In the case where the flow path is formed by a porous carrier, some of the sample may be caused to flow along the surface of the carrier that is in contact with the wick rather than through the body of the carrier, and so may not be brought into proper contact with the reagents and/or may flow faster than intended due to the flow at the surface not being sufficiently controlled by the capillarity of the porous material.

On the other hand, if, during or after sample application, the assay device is inverted, rotated, shaken, dropped or otherwise mishandled, at least a portion of the sample may not travel along the intended flow path, for instance it may be caused to flow in between the porous carrier and the casing of the assay device, or it may flow along the surface of the porous carrier. The uncontrolled flow of liquid sample may subsequently wet the downstream end of the assay flow path and, in so doing, flow may then occur along the assay flow path in the reverse direction. This will have an impact on the performance of the assay since the flow of reagents is not occurring in the intended direction.

Similarly, even if the device is held horizontally throughout the test, if the sample is applied at the far downstream end of the exposed portion of the wick where it enters the housing of the device and/or is applied in a high velocity stream, there is a risk that the sample will travel in an unintended direction. All these situations are referred to herein as flooding of the device, although devices that have been inverted immediately after taking up the correct amount of sample, and devices that have been both oversampled and inverted or mishandled, may be most susceptible to flooding. Flooding is undesirable because it could cause the assay to fail (i.e. no assay result is displayed to the user and the test is wasted) or, more seriously, could give rise to a false negative result.

This is especially an issue for assay devices that are designed to run on a relatively large volume of sample, and for those that use samples of low viscosity, for instance those that analyse urine, or a biological fluid that has been diluted with an aqueous fluid, e.g. to allow it to flow properly in the assay. It will be appreciated that this problem may be experienced with a wide range of assay devices other than the one described in EP 0,291,194.

Accordingly, the user is generally instructed to take care to apply only a certain volume of sample (e.g. by holding the wick in their urine stream for 5 seconds only or by dipping the wick up to a certain distance in their collected urine for 5 seconds only) and to handle the assay device in an appropriate manner (e.g. to hold it in a horizontal orientation whilst the assay is running and not to invert it at any stage after sample application).

Often the user is not a frequent user of this type of assay and is expected to interpret the procedure for performing the assay from reading instructions and observing diagrams which are provided with the assay. Unfortunately, however, the user may not always comply with the instructions, for instance due to misinterpreting them or even not reading them at all in their eagerness to use the device. When detecting analyte in a urine sample, the user may prefer to apply their urine to the sample application area directly from their urine stream ("midstream sampling") rather than collect their urine in a container first, but in practice they may experience difficulties in controlling the direction of their urine stream onto the wick and, especially for women (bearing in mind their anatomy), being able to see what they are doing when midstream sampling. When using the test by dipping the wick into a container of urine, they may dip it too deep such that the entire wick and some of the casing of the device is submerged, and urine enters the device in an uncontrolled fashion and amount. After applying the sample, the device may be accidentally dropped, or some users may be inclined to flick or shake the device in their anxiety for the result. All these factors and more mean that, despite the instructions, in reality flooding may still occur. Indeed, devices that are exposed to a midstream sample of urine are particularly renowned for flooding.

Certain solutions have been proposed to overcome the problem of flooding. For example, U.S. Pat. No. 6,277,650 and U.S. Pat. No. 6,046,057 describe single step assay devices comprising drainage vents spaced around a urine inlet port in a device intended to determine the presence of an analyte in a urine sample. These drainage vents are intended to minimise the build up of excessive urine within the casing at the sample receiving portion of the device. However, such drainage vents may not overcome the problem of flooding caused by inverting the device after the urine has been applied thereto. Even when a suitable amount of liquid sample is applied to the device, subsequently inverting, shaking or rotating the device can cause the liquid to flow through the device too quickly or along an incorrect flow path, thereby flooding the device.

In addition, U.S. Pat. No. 6,277,650 and U.S. Pat. No. 6,046,057 describe the provision of a rib member positioned within the casing of the device, which acts as a barrier preventing hydraulically driven urine from flowing into the portion of the device containing the assay components. The rib members may be integral with the casing of the device, or may be manufactured as separate components. An inherent problem with such rib members or barriers is that they are often unable to completely prevent entry of excess fluid into the portions of the device which contain the assay reagents. Assay devices of this nature are often manufactured at reduced cost (since, in many cases, the devices can be used only once) from plastic materials and are often assembled by joining together separate portions of the device via snap-fit, or other simple mechanical connections. Given these manufacturing considerations, it is difficult to produce a fluid impermeable barrier that can reliably prevent the flow of excess liquid into portions of the device which contain the assay reagents. For example, leaks often occur through snap-fit connections, or gaps may form around the barrier as a result of manufacturing tolerances. The problem is made more difficult by the fact that such devices need to allow at least some of the sample liquid to flow into the portion which contains the assay reagents, in order to carry out the assay and provide a result. Thus, such assay devices need to be manufactured with enough of a gap or opening between the sample receiving portion and the portion containing the assay reagents in order to work. It is difficult to ensure that this gap or opening will allow enough liquid through in order to complete the assay, whilst at the same time preventing too much liquid from flowing through and flooding the device and invalidating the assay result, particularly given that some users may invert or shake the device after having applied the liquid sample.

Thus, there is a need for an improved way of reducing the incidence of flooding of an assay device.

In a first aspect, the invention provides an assay device for detecting an analyte in a fluid sample, comprising a sample receiving member (1) fluidically connected to one or more components (2, 3) defining an assay flow path, at least one of which is a detection member (3) comprising an analyte detection zone (31), the assay flow path optionally comprising a control zone; wherein the device further comprises a sample-absorbing member (5) that does not form part of the assay flow path, and that is not completely downstream of the analyte detection zone (31) and/or the control zone if present.

In a second aspect, the invention provides an assay device for detecting an analyte in a fluid sample, comprising a sample receiving member (1) fluidically connected to one or more components (2, 3) defining an assay flow path, at least one of which is a detection member (3) comprising an analyte detection zone (31), wherein the device further comprises a sample-absorbing member (5) substantially downstream of the sample receiving member (1) that does not form part of the assay flow path.

Unless otherwise stated, all embodiments of the invention described herein apply equally to both aspects of the invention (except where this would give rise to inconsistency).

Figure 1:
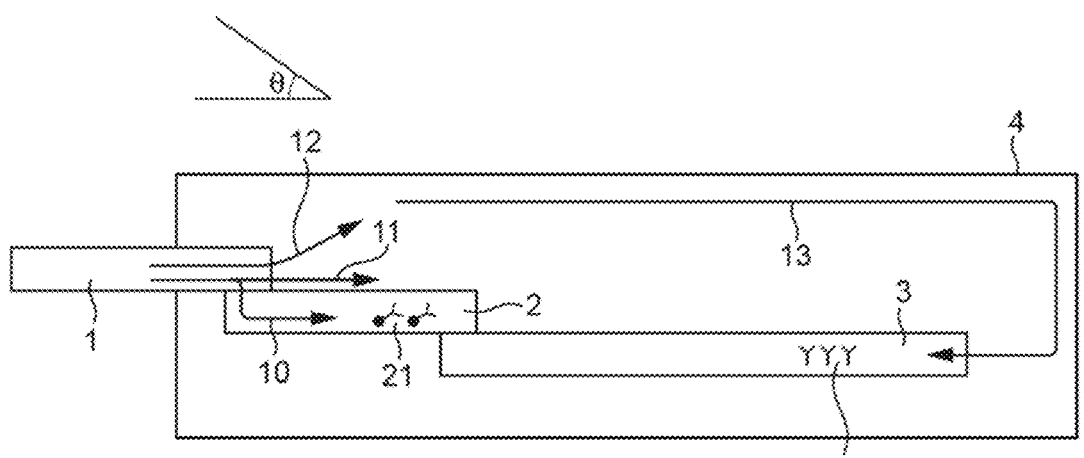
FIG. 1 illustrates a prior art assay device.

By "assay flow path" is meant the path along which the sample is intended to flow during performance of the assay. Flooding of the device, e.g. when the device is mishandled by the user or oversampled, tends to cause sample to flow outside of this assay flow path.

The sample-absorbing member does not form part of the assay flow path and so is not in the stream of the sample during normal functioning of the device, thus technically might not be considered to be "upstream" or "downstream" of components of the assay flow path. Herein, however, "upstream", when referring to the location of the sample-absorbing member relative to another part of the device, means it is closer to the sample receiving member than that part. Thus, during a flooding event which might create an abnormal flow path between the sample receiving member and that part, the sample-absorbing member would be located upstream of that part in the course of the abnormal flow path. Conversely, "downstream", when referring to the location of the sample-absorbing member relative to another part of the device, is meant to refer to it being positioned further away from the sample receiving member than that part, and so downstream from that part in the course of the abnormal flow path.

The sample receiving member is capable of receiving a liquid sample and of transferring the liquid to the start of the assay flow path. The sample receiving member may act as a sample capture means, and may be present in a sample receiving portion of the assay device. The sample receiving member may be an elongate strip. It may project from a housing that encloses the assay flow path. The sample receiving member is preferably made of a porous or fibrous material. In an embodiment, the device is adapted to transfer the sample from the sample receiving member to the start of the assay flow path without user-applied force. Preferably, the materials of the sample receiving member and component(s) of the assay flow path are selected such that the sample is transferable from the sample receiving member to the start of the assay flow path by capillary action only.

In an embodiment, the device is capable of being oversampled, for example, through continuous contact of the sample receiving member with an excess amount of sample (e.g. with a flow or container of urine) throughout the duration of the assay.

In an embodiment, the sample receiving member is macroporous. In an embodiment, the volume of sample needed to saturate the sample receiving member is greater than the volume of sample required to perform the assay.

The sample absorbing member may comprise one or more different materials. In an embodiment, the sample receiving member is a wick. The wick may comprise a material of relatively high capacity and high capillarity through which liquid can flow relatively easily. This may be relative to the other components of the assay flow path. This allows the wick to rapidly absorb a relatively large volume of sample liquid that is applied to the device, and also allows this volume of sample liquid to be transferred easily to the start of the assay flow path without being retained in the wick itself for a significant period of time. As a result, a wick that is inverted, shaken, rotated or dropped is particularly prone to allowing any sample liquid present in the wick to exit the wick rapidly and/or in an undesired direction.

In an embodiment, the wick is made of a fibrous material. The material may comprise fibres that are substantially aligned such that wicking of the sample liquid is mostly in a single direction along the length of these fibres. The alignment of these fibres may be substantially parallel with the direction of the assay flow path (at least at the upstream end of the latter). The directionality of the wick may be so strong that, during a flooding event, sample primarily exits from the far downstream end of the wick at the terminus of the fibres, with insignificant amounts of sample exiting the wick from a point upstream of the terminus of the fibres. The sample may drip from the end of the wick during a flooding event.

The wick material may be woven or unwoven.

In an embodiment, the sample receiving member has a wicking rate with water (along the direction of the member that is towards the assay flow path) of at least 0.5 cm/s, at least 1.0 cm/s, at least 1.5 cm/s, at least 2.0 cm/s, at least 2.5 cm/s, or at least 3.0 cm/s, and optionally less than 10.0 cm/s, or less than 5.0 cm/s.

Examples of suitable wick material include cellulose fibre, glass fibre, or fibrous material comprising polyester, nylon, cotton, mono-component fibre combinations thereof, or bi-component fibre combinations thereof.

The sample that is applied to the assay device is a fluid. The sample may naturally be a liquid, or may be a solid that has been pre-treated so as to be provided in liquid form before application to the device. For example, a solid sample such as faeces can be dissolved in a suitable solvent before being applied to the device. Alternatively, a liquid sample may be treated with another liquid (such as water or an aqueous solution) to reduce its viscosity and/or increase its volume before being applied to the device. The sample can be derived from any source and may be a bodily fluid, including blood, serum, plasma, saliva, sputum, ocular lens liquid, sweat, urine, milk, ascites liquid, mucous, synovial liquid, peritoneal liquid, transdermal exudates, pharyngeal exudates, bronchoalveolar lavage, tracheal aspirations, cerebrospinal liquid, semen, cervical mucus, vaginal or urethral secretions, and amniotic liquid. Depending upon the analyte of interest, other samples may be contemplated such as ones from industrial, environmental or agricultural sources.

In an embodiment, the sample is aqueous. In an embodiment, the sample has a viscosity of ≤2 mPa·s, ≤1.5 mPa·s, or ≤1 mPa·s at 25° C. In an embodiment, the sample is urine or a diluted bodily fluid.

During correct use of the device, the sample is conveyed along the assay flow path in which one or more reagents for the assay are found. The reagent(s) will vary according to the type of assay. The reagent(s) may interact with the analyte to form a detectable product, for example via a simple binding reaction to form an analyte-reagent complex, or via a chemical reaction.

The assay reagents may comprise mobilisable and immobilised assay reagents; the mobilisable reagents may be pre-deposited on the component(s) defining the assay flow path in a dry form. The "analyte detection zone", where a signal is formed indicating the presence and/or amount of analyte, may contain the immobilised assay reagents, and the mobilisable assay reagents may be initially provided in a zone ("assay reagent zone") upstream from the analyte detection zone. In the case where the assay comprises a sandwich assay, the assay reagent zone may bear a mobilisable labelled binding reagent for the analyte and, downstream from this, the analyte detection zone bears immobilised non-labelled binding reagent for the analyte. Of course, other assay formats such as a competition assay or inhibition assay are also possible, known to the skilled person and included within the scope of the invention. Another example is where the analyte is an enzyme, which is capable of cleaving the assay reagent to produce a cleavage product that is subsequently detected.

The component(s) defining the assay flow path may also contain one or more control reagents, which may be used in the conventional fashion to provide an indication at a "control zone" that the assay has run correctly. For instance, mobilisable labelled control reagents may be provided at an upstream location in the assay flow path (e.g. in the same location as the assay reagent zone), with immobilised control reagents in the control zone. The mobilisable control reagents may bind to the immobilised control reagents, and so accumulation of the label in the control zone affords a signal that the assay has run correctly. Typically, the control zone is located downstream from the analyte detection zone.

The assay flow path may be defined by an integral component, or by a plurality of fluidically connected components. For instance, the assay reagent zone may be provided on a first material (which may be a so-called "conjugate pad"), and the analyte detection zone may be provided on a downstream, fluidically connected, second material.

The component(s) defining the assay flow path may comprise any material capable of allowing the sample to flow from the sample receiving member to the assay reagent(s). The assay device may be configured as a lateral flow device, and the component(s) may comprise a porous, fibrous or bibulous carrier.

In an embodiment, the component(s) comprises a porous carrier, or a plurality of fluidically connected porous carriers. The porous carrier(s) may comprise any material suitable for conveying the sample to the assay reagent(s). The wicking rate of the sample along the assay flow path is preferably slower than the wicking rate of the sample through the sample receiving member.

Examples of the porous carrier material(s) include glass fibre, cellulose, nitrocellulose, paper, silica, porous synthetic polymers such as sintered PET, and material comprising polyester, nylon, cotton, mono-component fibre combinations thereof, or bi-component fibre combinations thereof. The porous carrier material(s) may be a woven or a nonwoven material.

In an embodiment, the porous carrier(s) comprise glass fibre and/or nitrocellulose. In an embodiment, the components defining the assay flow path comprise a glass fibre pad on which the assay reagent zone is located, and a nitrocellulose strip on which the analyte detection zone is located, the glass fibre pad being fluidically connected to and upstream of the nitrocellulose strip.

At least a portion of the sample receiving member may overlap the porous carrier. In this situation, at least some of the sample liquid exiting the sample receiving member may be caused to flow along the surface of the porous carrier during a flooding event. Sample tends to flow more quickly across this surface. Assay reagents may be located within the porous carrier, such that sample flowing along the surface is not fully brought into contact with these assay reagents.

An example of this configuration in a prior art device is illustrated in FIG. 1. The device contains a sample receiving member 1 and components defining an assay flow path consisting of two fluidically connected strips 2 and 3. The assay flow path is enclosed in a housing 4 and the sample receiving member 1 projects from the housing 4. The downstream end of the sample receiving member 1 overlaps the upstream end of strip 2, which is a conjugate pad bearing labelled mobilisable assay reagents 21 in a assay reagent zone. The downstream end of the conjugate pad 2, in turn, overlaps the upstream end of strip 3, which bears immobilised non-labelled assay reagents 31 in an analyte detection zone.

Under normal sampling conditions, the sample flows along the path of arrow 10 (part of the assay flow path). However, when too much sample is applied and/or the device is held off-horizontal (usually $\theta=90°$ or less) with the sample receiving member uppermost, some of the sample can exit the sample receiving member along the path of arrow 11 (flooding direction) and run along the surface of the pad 2. If the device is held with the sample receiving member uppermost but angled further off the vertical ($90°\leq\theta\leq180°$), sample may even exit in a direction away from the pad 2, e.g. as shown by arrow 12 (flooding direction). In addition, sample may run along the inside of the upper case part and then drop down and start running along the assay flow path in the reverse direction (see e.g. arrow 13).

The present invention uses a sample-absorbing member that is capable of absorbing and retaining (for a sufficient period of time) excess sample liquid which enters the device, and/or liquid which flows into the wrong part of the device, thereby increasing the tolerance of the device to incorrect usage and reducing the incidence of a false result or no result being obtained. It is located outside of the intended, assay flow path of the sample. In this way, it should be contrasted with any further absorbent substance which may be located towards the terminus of the assay flow path, downstream of all the assay reagents in the assay device, which is intended to assist in drawing sample through the correct flow path and is referred to herein (and commonly in the art) as a "sink pad". In other words, when a sink pad is present which is fluidically connected to the rest of the flow path, this is considered as one of the components defining the assay flow path.

When the device does not contain a control zone, the sample-absorbing member is located not entirely downstream of the analyte detection zone. In other words, at least a portion of the sample-absorbing member is upstream of, or level with, the analyte detection zone. Thus, during a flooding event, at least some of the sample will reach the sample-absorbing member and be absorbed before it can reach the analyte detection zone. In this manner, it can be further distinguished from known devices unrelated to the present invention, in which an absorbent pad is not fluidically connected to the assay flow path at the start of the assay, but is moved into contact with the distal end of the assay flow path during the course of the assay, in order to function as a sink pad at that time (e.g. WO 2005/029073). Other devices are known that bear an absorbent material at the terminus distal from the sample receiving member and unconnected with the assay flow path, which are similarly unrelated to the present invention; the damage to the assay has already been done by the time the sample reaches such absorbent material.

When the device does contain a control zone, the sample-absorbing member is located not entirely downstream of the analyte detection zone, and/or not entirely downstream of the control zone. In an embodiment, the control zone is downstream of the analyte detection zone, and at least a portion of the sample-absorbing member is upstream of, or level with, the control zone. This increases the chance that the user is alerted to a flooding event following the lack of, or abnormality of, a signal at the control zone. Preferably, however, the control zone is downstream of the analyte detection zone and at least a portion of the sample-absorbing member is upstream of, or level with, the analyte detection zone, such that a signal is less likely to form at either zone when flooding occurs.

In an embodiment, the sample-absorbing member is located upstream of all the assay reagents (and optionally upstream of all the control reagents, if present). In another embodiment, the sample-absorbing member is located entirely upstream of the analyte detection zone but not entirely upstream of the assay reagent zone. For instance, the downstream end of the sample-absorbing member may be located at the same distance downstream as some mobilisable labelled binding reagents on the assay flow path, or the sample-absorbing member may straddle the assay reagent zone.

The sample absorbing member is preferably located such that it absorbs excess sample during a flooding event and allows the flow of an amount of sample to the analyte detection zone sufficient to detect the analyte in the sample. In other words, sample that is flowing outside of the flow path is absorbed and retained by the sample absorbing member. Sample that is flowing along the flow path in the desired manner and amount is not absorbed by the sample absorbing member, and is able to flow along the flow path to the detection member and give an accurate result at the detection zone. The sample absorbing member prevents excess and/or incorrectly flowing sample from interfering with the flow path components, such that an accurate result is more likely to be obtained even when the device is mishandled.

In an embodiment of the first aspect of the invention, at least a portion of the sample-absorbing member is downstream of the sample receiving member. Preferably, the sample-absorbing member is substantially downstream, preferably entirely downstream, of the sample receiving member. In another embodiment of this aspect, the sample-absorbing member is positioned at the same distance downstream as the downstream end of the sample receiving member. This latter embodiment may be useful when the sample receiving member does not have very strong directionality such that sample is liable to exit it prior to its terminal downstream edge, during a flooding event, and be absorbed straight away by the sample-absorbing member.

The sample-absorbing member may comprise any material capable of absorbing and retaining the sample liquid for a sufficient period of time. In an embodiment, the sample-absorbing member comprises a porous, fibrous or bibulous material. For instance, the sample-absorbing member may be a sponge or a foam material, a porous fibre material, or a porous plastics material such as sintered polyethylene. The sample-absorbing member may be a micro-machined plastics material engineered to have capillary channels to be able to uptake the sample, or it may comprise elongate structures (like plastic "teeth" or the fibres of a brush) angled roughly orthogonal to the assay flow path, which trap sample therebetween. Alternatively the capillary channels may lie substantially parallel to the assay flow path.

The sample-absorbing member may be integral with the housing or other parts of the device, or a separate member therefrom. For instance, it may be a portion of a graded material through which insignificant amounts of sample would flow during normal sampling conditions, and a different portion of that graded material forms a component of the assay flow path. Preferably, however, it is non-integral with any components of the assay flow path. In an embodiment, it is non-integral with the housing. Preferably, it is a separate member from any other part of the device. It may be swellable upon uptake of the sample, such as a hydrogel, or non-swellable. The sample-absorbing member may comprise a woven or a non-woven material. The sample-absorbing member may comprise one or more of any of these materials, in any combination. Preferably, it is hydrophilic.

The absorbent capacity and rate of absorption of the sample-absorbing member may be affected by various factors, such as its size, density, the average size of its pores and the pore size distribution. Clearly, the desirable values of these parameters will vary according to the basic design of the device, which affects e.g. how much space there is to accommodate the sample-absorbing member, the maximum likely volume of excess sample that needs to be absorbed, the fastest sample flow rate likely to be seen during a flooding event, and so on, and the invention is not limited to any particular such values. Similarly, the sample-absorbing member may be of any suitable shape, for instance an elongate strip.

Figure 2:
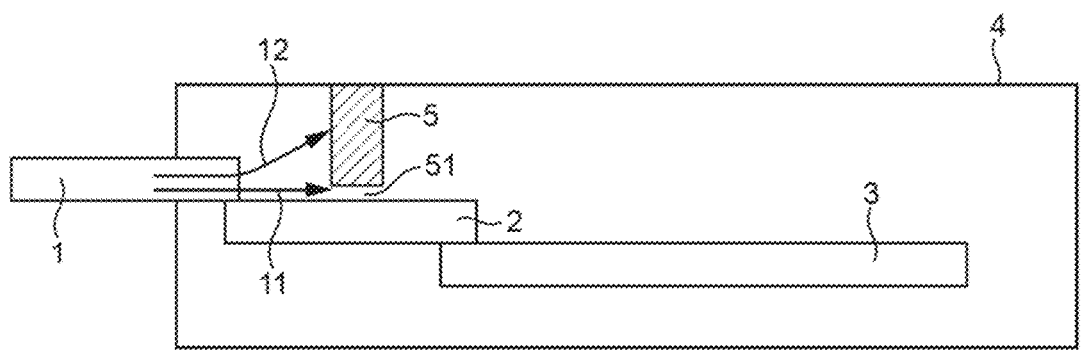
FIG. 2 illustrates one assay device in accordance with the invention, in which the sample-absorbing member is spaced apart from the components defining the assay flow path and from the sample-receiving member.

As exemplified by the configuration of FIG. 2, the sample-absorbing member 5 may be located adjacent to but not touching the component(s) defining the assay flow path 2 or the sample receiving member 1, so as not to be fluidically connected to either entity. For instance, it may be spaced apart from the component(s) defining the assay flow path and from the sample receiving member by an air gap 51 or via an intermediate, sample-impermeable material. It may be held in position by any suitable means, for instance by attachment to the upper inside face of the housing 4, or through features within the housing such as by light pinching between rib members. Preferably, the sample-absorbing member, if compressible, does not suffer any significant compression inside the device, as this would restrict its sample absorption capability.

In this way, the sample-absorbing member may be capable of absorbing sample that does not flow in the intended region of the device. For instance, when a user angles the device (with $90°\leq\theta\leq180°$) after having applied the sample so that the sample receiving member points upwards, the sample may flow out of the sample receiving member in a direction away from the intended, assay flow path and may drop under the force of gravity towards the sample-absorbing member instead (c.f. arrow 12). In this embodiment, it will be evident that any type of absorbent material could be used for the sample-absorbing member, and it will have a positive influence in reducing the incidence of flooding without adversely affecting the assay under correct sampling conditions.

In an embodiment, an air gap 51 is present but the size of the air gap is sufficiently small that droplets of sample liquid which may be forced out of the sample receiving member during inversion or shaking of the device could not pass through the air gap along the path of arrow 11 without contacting the sample-absorbing member 5, thereby becoming at least partially absorbed by the sample-absorbing member.

Alternatively, the sample-absorbing member may be positioned so as to be touching and fluidically connected to one or more of the component(s) defining the assay flow path and/or the sample receiving member. In this embodiment, the device is desirably adapted such that the sample-absorbing member does not adversely affect the running of the assay when the device is used correctly. For instance, the device should be adapted to prevent the sample-absorbing member from drawing a significant proportion of the sample liquid directly from the sample receiving member or from the component(s) defining the assay flow path and away from the intended direction towards the assay reagents, under normal sampling conditions. The sample-absorbing member need not necessarily be completely prevented from drawing any sample directly from the sample receiving member or from the component(s) defining the assay flow path; the device may be adapted such that a small amount of sample is absorbable by this route without adversely affecting the assay under normal sampling conditions, and such that the sample-absorbing member retains a capacity for absorbing further sample during a flooding event. Whilst a very small proportion of the sample (e.g. <10%, <5% or <2%) may enter the sample-absorbing member during normal running of the device, the sample-absorbing member is not considered to form part of the assay flow path.

Ways of preventing the sample-absorbing member from adversely affecting the normal running of the assay include appropriate selection of the relative capillarity of the sample-absorbing member and the component(s) that it contacts (at least at the area of contact), appropriate selection of the surface area of the sample-absorbing member in contact with the component(s), and appropriate selection of the overall size/absorbent capacity of the sample-absorbing member.

Figure 3A:
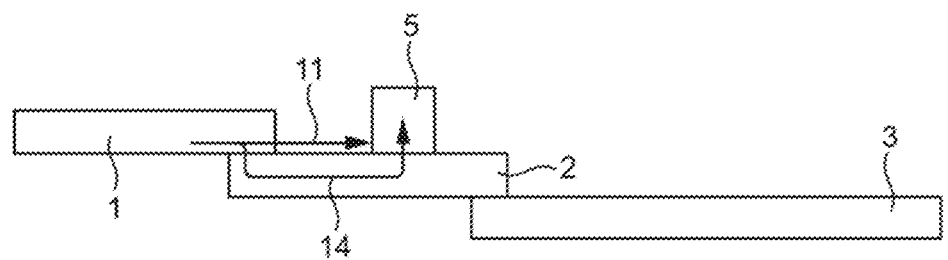
FIG. 3a illustrates another assay device in accordance with the invention, in which the sample-absorbing member is fluidically connected to the components defining the assay flow path but spaced apart from the sample-receiving member.

In an embodiment, the sample-absorbing member is spaced apart from the sample receiving member but touches the surface of the component/one of the components defining the assay flow path, this component comprising a porous carrier. The sample-absorbing member is capable of absorbing, by capillary action, any sample liquid flowing across the surface of the carrier, as exemplified by the configuration shown in FIG. 3*a* (c.f. arrow 11). Sample flow from the main body of the porous carrier 2 to the sample-absorbing member 5 (c.f. arrow 14) may, for instance, be minimised by ensuring that the sample-absorbing member has a lower capillarity than that of the porous carrier. Either the whole sample-absorbing member may be of lower capillarity, or the sample-absorbing member may be a graded material (or comprise conjoined materials of differing capillarities) with a lower capillarity end positioned in contact with the porous carrier and a higher capillarity opposite end for absorbing sample during flooding. Alternatively, the lower and higher relative capillarity may vary across the width of the sample absorbing member, for example, in order to ensure more sample flows through the centre of the member than through the edge areas. Another option would be to ensure that the surface area of the sample-absorbing member in contact with the porous carrier is relatively small, but the sample-absorbing member still retains a sufficient absorbent capacity (e.g. by being tall), if the sample-absorbing member has an end in contact with the porous carrier that is of equal or higher capillarity than the capillarity of the porous carrier. Thus the capillarity and dimensions of the sample-absorbing member can be selected in conjunction with one another to control the speed of draw of fluid from the assay flow path during normal running conditions, such that the assay is not adversely affected.

Figure 3B:
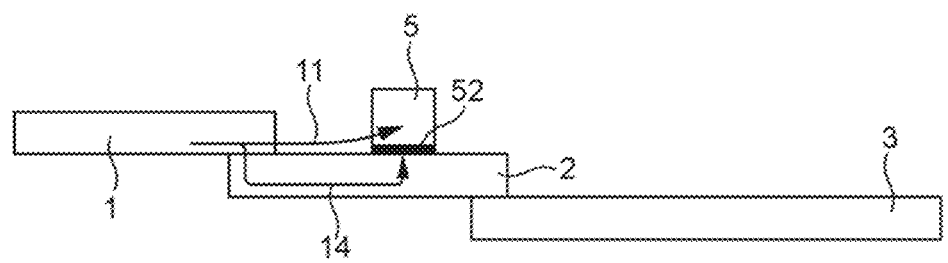
FIG. 3b illustrates a further assay device in accordance with the invention, in which the sample-absorbing member is spaced apart from the sample-receiving member and not fluidically connected to the components defining the assay flow path, although a fluidic connection to the latter may be made during a flooding event.

In another embodiment, exemplified by the configuration shown in FIG. 3b, a thin, sample-impermeable barrier 52 (such as a thin film) may separate the porous carrier 2 from the sample-absorbing member 5, such that the latter is not fluidically connected to the component defining part or all of the assay flow path when the device is in the dry state (c.f. arrow 14). A fluidic connection may be made along the direction of arrow 11 during a flooding event that causes sample to flow along the surface of the porous carrier. The barrier 52 should be sufficiently thin to allow this to happen; if it is too thick it will simply act as a spacer in the manner described above in connection with FIG. 2. Preferably the height of the film is ≤2 mm or ≤1 mm.

If the sample-absorbing member is produced in a way that leaves stray fibres/pieces of material protruding from its sides, sample may be able to bypass the sample-impermeable barrier under normal sampling conditions if the latter only covers the base of the sample-absorbing member and no more. Under these circumstances it may be advantageous to make the sample-impermeable barrier extend beyond the base of the sample-absorbing member; during a flooding event, sample can run along the surface of the porous carrier, over and along the surface of the barrier and then be drawn into the sample-absorbing member, but the assay is adequately protected under normal sampling conditions.

Similarly, the sample-absorbing member may abut the end of the sample receiving member but be separated from direct contact with it by a barrier, such as a film that is impermeable to the sample. Alternatively, the sample-absorbing member is in direct contact with the sample receiving member but substantial sample flow from the latter to the former under normal sampling conditions is minimised in the same ways discussed above.

Figure 4A:
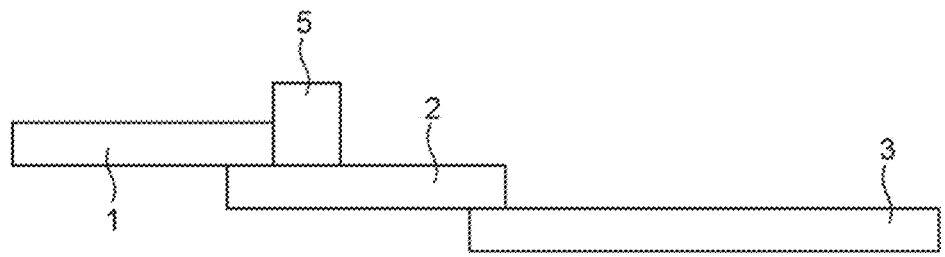
FIGS. 4a to 4f illustrate various other possible configurations of assay devices in accordance with the invention.
Figure 4B:
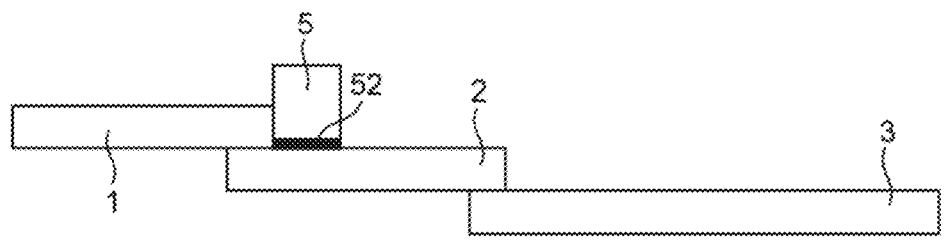
Figure 4C:
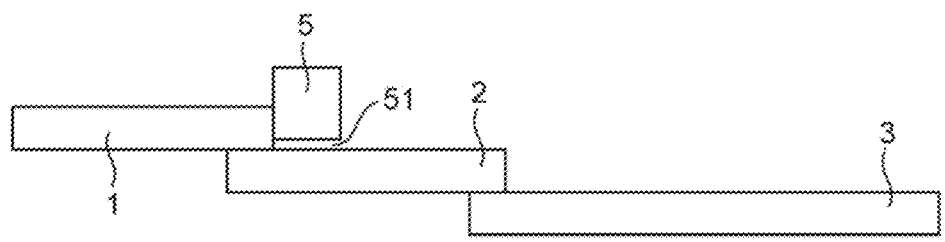
Figure 4D:
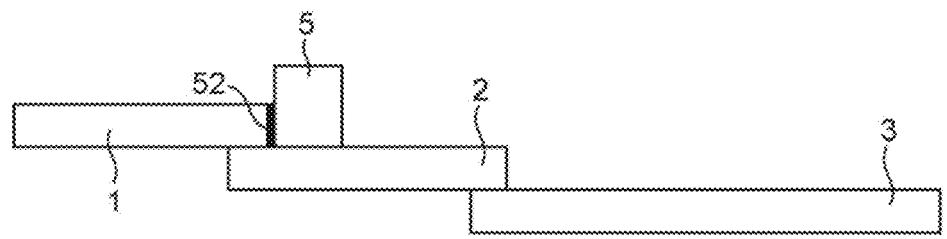
Figure 4E:
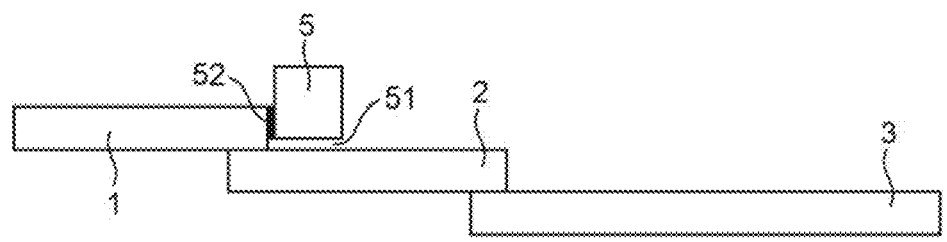
Figure 4F:
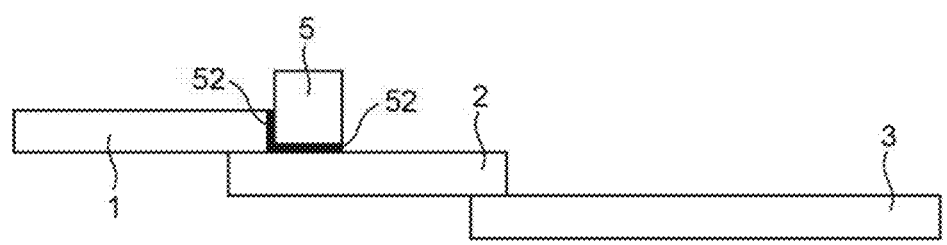

Various possible configurations are illustrated in FIGS. 4a-4f; of these six, those of FIGS. 4a and 4b are preferred.

The sample-impermeable barrier may be made of any suitable material, for instance a plastics material or a metal. The sample-impermeable barrier may be hydrophobic or hydrophilic; in an embodiment it is hydrophobic. More hydrophilic barriers are more easily wetted by (aqueous) samples and so will be more easily overcome during a flooding event. Thus the thickness and relative hydrophilicity of the barrier can be selected in conjunction with each other to tailor the absorption of sample by the sample-absorbing member during flooding events. Advantageously, the sample-impermeable barrier is an adhesive with the additional function of helping to hold the sample-absorbing member in position.

The relative capillarity of two components can be determined experimentally by known, simple techniques. For instance, the components can be held in the same container of dyed water, and the relative rates of progress of the dye fronts up the components can be observed. In some cases, there may be a correlation between capillarity and density.

In an embodiment, the sample-absorbing member has a capillary wicking rate with water of less than 10 cm/s, less than 6 cm/s, less than 5 cm/s, less than 4 cm/s, less than 3 cm/s, less than 2 cm/s, or less than 1.5 cm/s, and optionally greater than 0.5 cm/s or greater than 1.0 cm/s. The sample-absorbing member may have a water absorption capacity of 0.01-5 g/cm$^3$, 0.05-4 g/cm$^3$, 0.1-3 g/cm$^3$, 0.3-2 g/cm$^3$, 0.5-1.5 g/cm$^3$, 0.7-1.2 g/cm$^3$, or 0.8-1.0 g/cm$^3$. It may have a density of 0.01-0.5 g/cm$^3$, 0.02-0.4 g/cm$^3$, 0.03-0.3 g/cm$^3$, 0.04-0.2 g/cm$^3$, 0.05-0.15 g/cm$^3$, 0.06-0.13 g/cm$^3$, or 0.07-0.11 g/cm$^3$. The sample-absorbing member may have an absolute water absorption capacity of >0.05 ml, >0.1 ml, >0.2 ml, or >0.5 ml.

The sample-absorbing member does not contain any of the assay reagents. It may, however, contain other reagents, such as reagents for indicating that it has absorbed more than a predetermined amount of sample. For instance, if the sample-absorbing member were to become completely saturated with sample under extreme flooding conditions, it might not fully prevent the device from failing, and under these circumstances it would be useful to indicate this failure to the user. As opposed to providing a generalised error message, it may indicate specifically that the error is due to extreme oversampling, so the user should retest taking care not to oversample the device. An example of the way this could be implemented is by providing an indicator, which changes colour in the presence of sample, located in a position where it would not be wetted until the predetermined amount of sample has been absorbed for a device undergoing a typical flooding event; this colour change may be observed through a window in the device. Alternatively, the sample-absorbing member could be provided with other means to detect the absorption of too high an amount of sample, such as a conductivity detection system positioned to detect the change in conductivity when it is fully wetted.

The assay device may further comprise a sink pad located downstream from all the assay reagent(s) and any control reagent(s) present in the assay flow path, typically at the terminus of the assay flow path. The sink pad encourages continued flow of the sample along the assay flow path, by wicking sample from the other, upstream component(s) defining the assay flow path and retaining it within the sink pad. The sink pad may comprise any suitable absorbent or bibulous material as is known in the art, such as cellulose, cotton and/or glass fibre.

The invention is not limited to the detection of any particular analyte. For instance, the analyte may be of a mammalian, especially of a human origin, or of a bacterial or viral origin. More than one analyte may be detected. In the case where the device includes more than one analyte detection zone, at least a portion of the sample-absorbing member is preferably upstream of, or level with, at least one of the analyte detection zones.

The presence and/or amount of the analyte(s) may be indicative of any clinical, physiological or medical condition. The analyte(s) may, for example, be a toxin, pollutant, organic compound, protein, enzyme, peptide, microorganism, bacterium, virus, amino acid, nucleic acid, carbohydrate, hormone, steroid, vitamin or drug. In an embodiment, the analyte(s) is a hormone. In an embodiment, the analyte(s) is human chorionic gonadotropin (hCG), luteinizing hormone (LH), estrone-3-glucuronide (E3G), or a fragment or isoform thereof.

The assay device may provide a qualitative, semi-quantitative or quantitative detection of the analyte of interest. The result of the assay can be interpreted by the user by viewing the analyte detection zone(s) and the control zone(s) if present measured by an optical or other measuring system and the result can be displayed in any known suitable form, such as via a digital display or an alternative visual signal of the assay result.

The assay device may detect more than one analyte, for instance via the inclusion of a separate detection zone for each analyte in the assay flow path. Alternatively, the assay device may comprise a plurality of separate assay flow paths; each may have its own associated sample-absorbing member, or a single sample-absorbing member may be shared between assay flow paths (e.g. if the assay flow paths are arranged side by side). The assay flow paths may share a single sample-receiving member. The device may use a plurality of separate assay flow paths in the quantitation or semi-quantitation of a single analyte.

In use, the sample may be applied directly to the device. When the sample liquid is a bodily fluid, the device can be used to collect the liquid sample directly from a subject. For example, the device can be used to collect a mid-stream urine sample.

Alternatively, the sample may be subjected to a liquid pre-treatment step before being exposed to the assay device. The liquid pre-treatment step may comprise one or more of, but not limited to, a dilution, a liquid suspension, an extraction, a binding reaction, a biochemical reaction, a chemical reaction, a lytic reaction, a buffering or a treatment with a surfactant. Thus, as discussed above, the liquid pre-treatment step may be used in order to ensure that the sample is applied to the device in liquid form, applied as a sufficiently low viscosity liquid, and/or to ensure that the analyte of interest is presented in a form which will allow the analyte to react or interact with the one or more assay reagents.

The assay device may further comprise a sampling means for obtaining a sample and transferring the sample to the sample receiving member, after any desired pre-treatment steps have been carried out. The sampling means may be adapted to receive a sample of bodily fluid from a subject.

The prior art documents mentioned herein are incorporated to the fullest extent permitted by law.

The dimensions of the assay devices illustrated in the Figures are exemplary only. It will be appreciated that the dimensions and materials of the assay device of the invention can be varied as desired.

The invention will be further described and illustrated in the following non-limiting examples.

Example 1

Reduction of Flooding Under Various Sampling Conditions

Multiple sets of single step lateral flow pregnancy test devices were prepared, of the type described in EP 0,291,194. The sample receiving member was a nylon/polyester bicomponent fibre wick, and the assay flow path was defined by a glass fibre conjugate pad overlapping a nitrocellulose strip. Blue latex-labelled anti-hCG antibody and blue-latex-labelled rabbit IgG antibody were deposited on the conjugate pad; the test zone on the nitrocellulose strip contained immobilised non-labelled anti-hCG antibody and the control zone contained immobilised non-labelled goat anti-rabbit IgG antibody. When urine containing a sufficient amount of hCG to indicate pregnancy is applied to the wick and the assay runs correctly, a blue line is expected to form in the test zone and in the control zone, caused by the immobilisation of the blue latex in those areas via a "sandwich" or other binding reaction.

Different sets of devices were each provided with a sample-absorbing member which was a pad made of a hydrophilic, polyolefin-based porous fibre material and having a density as specified in Table 1 below. The sample-absorbing pad was cuboid in shape and had the dimensions specified. It rested on the conjugate pad and spanned the full internal width of the device but was not in contact with the wick. No barrier film was present between the sample-absorbing pad and the conjugate pad, but the sample-absorbing pad had a lower capillarity than the conjugate pad. The sample-absorbing pad with a density of 0.1 $g/cm^3$ had a water absorption capacity of 0.92 $g/cm^3$; the absorption capacity of the other sample-absorbing pad was unreported. The wick was 2.0 mm thick. The remaining (control) set of devices was identical to the other sets except that it did not contain any sample-absorbing pad.

The devices were tested according to the following protocols:

Normal sampling: the device was placed vertically, wick end first, into a container holding 27 ml of a standard 0.1 M phosphate-buffered saline solution with sodium azide plus 0.1% ovalbumin containing 25 mIU/ml hCG (a level of hCG which would be expected to test positive for pregnancy on the device), with half of the exposed wick immersed, and held there for 5 seconds. The device was then removed from the sample liquid, laid flat and the assay was allowed to run. After three minutes, the device was observed for the presence of test and control lines.

Moderate abnormal sampling: the device was placed vertically, wick end first, into a container holding 27 ml of the above solution containing 25 mIU/ml hCG, with all of the exposed wick up to the edge of the plastic moulding immersed, and held there for 5 seconds. The device was then removed from the sample liquid and rotated 180 degrees over the course of 5 seconds so as to be held vertically with the wick end pointed uppermost, and held constant in this inverted position. After three minutes, the device was observed for the presence of test and control lines.

Severe abnormal sampling: the device was tested as for the moderate abnormal sampling protocol, except that it was held in the sample liquid so that all of the exposed portion of the wick and at least 5 mm of the plastic moulding was immersed.

The results are shown in Table 1 below.

As can be seen from a comparison of experiment C1 using the control devices (having no sample-absorbing pad), and experiments E1 and E4 using two embodiments of devices of the invention, the latter do not adversely affect the running of the assay under correct sampling conditions. Experiment C2 shows that the control devices gave rise to false negatives in 5 out of 20 cases when moderately missampled, whereas both devices of the invention solved this problem as evidenced by experiments E2 and E5. Experiment C3 shows that the control devices completely failed under severe missampling conditions, but a significant improvement was seen with both devices of the invention under the same conditions, as evidenced by experiments E3 and E6.

TABLE 1

| Experiment | C1 | C2 | C3 | E1 | E2 | E3 | E4 | E5 | E6 |
| --- | --- | --- | --- | --- | --- | --- | --- | --- | --- |
| Pad density ($g/cm^3$) | n/a | n/a | n/a | 0.07 | 0.07 | 0.07 | 0.10 | 0.10 | 0.10 |
| Pad size (l) × (w) × (h) (mm) | n/a | n/a | n/a | 22 × 4.5 × 4.5 | 22 × 4.5 × 4.5 | 22 × 4.5 × 4.5 | 22 × 4.5 × 4.5 | 22 × 4.5 × 4.5 | 22 × 4.5 × 4.5 |

TABLE 1-continued

| Experiment | C1 | C2 | C3 | E1 | E2 | E3 | E4 | E5 | E6 |
|---|---|---|---|---|---|---|---|---|---|
| Sampling protocol | Normal | Moderate abnormal | Severe abnormal | Normal | Moderate abnormal | Severe abnormal | Normal | Moderate abnormal | Severe abnormal |
| No. of devices that formed test line | 30/30 | 15/20 | 0/13 | 30/30 | 20/20 | 38/49 | 20/20 | 25/25 | 17/25 |
| No. of devices that formed control line | 30/30 | 20/20 | 0/13 | 30/30 | 20/20 | 47/49 | 20/20 | 25/25 | 25/25 |

Upon inspection of the interior of the devices that failed to form a test and/or control line, an excess of liquid could be seen on the nitrocellulose strip and within the internal components of the casing, i.e. the failure was due to flooding.

TABLE 2

| Experiment | C1 | C3 | E6 | E7 | E8 | E9 | E10 | E11 | E12 |
|---|---|---|---|---|---|---|---|---|---|
| Pad density (g/cm$^3$) | n/a | n/a | 0.10 | 0.10 | 0.10 | 0.10 | 0.10 | 0.10 | 0.10 |
| Barrier film? | n/a | n/a | no | no | yes | no | yes | no | yes |
| Pad size (l) × (w) × (h) (mm) | n/a | n/a | 22 × 4.5 × 4.5 | 22 × 9 × 4.5 | 22 × 9 × 4.5 | 22 × 9 × 4.5 | 22 × 9 × 4.5 | 22 × 9 × 4.5 | 22 × 9 × 4.5 |
| Sampling protocol | Normal | Severe abnormal | Severe abnormal | Normal | Normal | Severe abnormal | Severe abnormal | Very Severe abnormal | Very Severe abnormal |
| No. of devices that formed test line | 30/30 | 0/13 | 17/25 | 10/10 | 10/10 | 10/10 | 10/10 | 15/15 | 14/15 |
| No. of devices that formed control line | 30/30 | 0/13 | 25/25 | 10/10 | 10/10 | 10/10 | 10/10 | 15/15 | 15/15 |

Example 2

The experiments of Example 1 were repeated with modifications to determine the effects of using a larger sample-absorbing pad and of incorporating a sample-impermeable barrier film between the sample-absorbing pad and the conjugate pad. An additional protocol was used as well:

Very severe abnormal sampling: the device was tested as for the severe abnormal sampling protocol, except that it was held in the sample liquid so that all of the exposed portion of the wick and at least 15 mm of the plastic moulding was immersed in the sample.

The results are shown in Table 2 below.

Experiments E7 and E8 confirm that the larger pad of density 0.1 g/cm$^3$ does not adversely affect the assay under normal sampling conditions, with or without the barrier film present. A comparison of experiments E6, E9 and E10 shows that the larger pad improves the performance of the device further, under severe abnormal sampling conditions, with or without the barrier film present. This improved performance is maintained even under more extreme abnormal sampling conditions (see experiments E11 and E12), although in this instance the version with the barrier film performed slightly worse than the version without the barrier film, exhibiting just one false negative result out of fifteen. In this embodiment, therefore, it is clear that a barrier film is not necessary, although it can be anticipated that with some higher density/higher capillarity sample-absorbing pads, the use of a barrier film would present an advantage.

Example 3

Performance Under Midstream Sampling Conditions

Experiments C1 and E1 were repeated but using a model of normal, midstream, sampling conditions as opposed to a dip protocol. Specifically, a pump was set up to deliver a stream of sample from a reservoir through a nozzle in an attempt to simulate sampling from a mid-stream source. Each device was held with the wick pointing downwards at a 60 degree angle from the horizontal and a 700 ml/min stream of the solution containing 25 mIU/ml hCG was directed vertically at the centre of the exposed portion of the wick for 2 seconds from the nozzle held 5 cm from the wick. The device was subsequently laid flat and observed for the appearance of test and control lines after 2 minutes.

All the devices in both sets (with and without the sample-absorbing pad) ran correctly and formed the expected test and control lines. This confirms that the sample-absorbing pad does not adversely affect the assay under normal, midstream sampling conditions.

Example 4

Use of Different Absorbent Materials

Devices were assembled as in example E1 but using a variety of different materials for the sample-absorbing pad, one of which was a Medisponge® material having a thin polyurethane film (sample-impermeable barrier) on its underside separating it from direct contact with the glass fibre conjugate pad. Another set of devices was assembled as in example C1.

The assay was run on half the devices in each set using the moderate abnormal sampling protocol set out above, except that the wicks were immersed in the sample containing 25 mIU/ml hCG prepared as above for twice as long (10 seconds), and the devices were held in the inverted position for 60 seconds before being observed for the presence of test and control lines. For the other half of the devices, they were held horizontally throughout the test and 900 µl of the solution containing 25 mIU/ml hCG was pipetted onto the wick. The devices were observed after 2 minutes for the appearance of the expected test and control lines.

All the control devices (having no sample-absorbing pad) formed the expected test and control lines under the normal sampling conditions, whereas they formed control lines but no clear test lines under the abnormal sampling conditions (i.e. exhibited false negatives due to flooding). On the other hand, all the devices having a sample-absorbing pad formed clear test and control lines under both types of sampling conditions.

The invention claimed is:

1. A lateral flow assay device for detecting an analyte in a fluid sample, comprising:
   a sample-receiving member (1) fluidically connected to one or more components (2, 3) defining an assay flow path extending in a downstream direction from sample-receiving member (1) to the one or more components (2, 3), at least one of which is a detection member (3), the one or more components (2, 3) comprising
   an assay reagent zone (21),
   an analyte detection zone (31) located substantially downstream from the assay reagent zone (21),
   one or more mobilizable assay reagents pre-deposited in the assay reagent zone, the one or more mobilizable assay reagents being in a dry form, and
   one or more immobilized assay reagents in the analyte detection zone (31);
   wherein the device further comprises a sample-absorbing member (5) located substantially downstream of the sample-receiving member (1), which does not form part of the assay flow path, and is not completely downstream of the analyte detection zone (31).

2. The lateral flow assay device of claim 1, wherein the sample-absorbing member (5) is entirely downstream of the sample-receiving member (1).

3. The lateral flow assay device of claim 1, wherein the sample-receiving member (1) is a wick.

4. The lateral flow assay device of claim 1, wherein the one or more components defining the assay flow path (2, 3) comprise a porous material or a plurality of fluidically connected porous materials.

5. The lateral flow assay device of claim 1, wherein the one or more mobilizable assay reagents (21) are borne by a component of the assay flow path which comprises a first porous material (2), and the one or more immobilized assay reagents (31) are borne by the detection member (3) which comprises a second porous material, wherein the first porous material is fluidically connected to the second porous material (3).

6. The lateral flow assay device of claim 5, wherein at least a portion of the sample-absorbing member (5) is not downstream of the assay reagent zone (21).

7. The lateral flow assay device of claim 1, wherein the sample-absorbing member (5) directly contacts one or more of the components defining the assay flow path (2, 3), and is adapted to absorb sample flowing along the surface of the one or more components defining the assay flow path (2, 3).

8. The lateral flow assay device of claim 7, wherein the sample-absorbing member (5) has a lower capillarity than the capillarity of the one or more components defining the assay flow path (2, 3) that it contacts.

9. The lateral flow assay device of claim 1, wherein the sample-absorbing member (5) is separated from one or more of the components defining the assay flow path (2, 3) by a sample-impermeable barrier which has a thickness and hydrophilicity sufficient to allow sample flowing along the surface of the one or more components defining the assay flow path (2, 3) to be absorbed by the sample-absorbing member (5).

10. The lateral flow assay device of claim 1, wherein the sample-absorbing member (5) does not directly contact the sample-receiving member (1).

11. The lateral flow assay device of claim 1, wherein the sample-absorbing member (5) has a density of 0.01-0.5 g/cm$^3$, 0.02-0.4 g/cm$^3$, 0.03-0.3 g/cm$^3$, 0.04-0.2 g/cm$^3$, 0.05-0.15 g/cm$^3$, 0.06-0.13 g/cm$^3$, or 0.07-0.11 g/cm$^3$.

12. The lateral flow assay device of claim 1, adapted to detect an analyte in a sample that has a viscosity of <2 mPa·s, <1.5 mPa·s, or <1 mPa·s at 25° C.

13. The lateral flow assay device of claim 1, wherein the sample is urine.

14. The device of claim 1, the one or more components (2, 3) further comprising
   a control zone located downstream from the analyte detection zone (31).

15. The device of claim 1, further comprising:
   a housing (4) enclosing the assay flow path, the sample-receiving member (1) projecting from the housing (4).

16. The device of claim 1, wherein the sample-absorbing member (5) is substantially fixed relative to the assay flow path.

17. The lateral flow assay device of claim 1, wherein the sample-absorbing member (5) is upstream of the analyte detection zone (31).

18. The lateral flow assay device of claim 1, wherein the sample-absorbing member (5) is entirely downstream of the sample-receiving member (1) and is upstream of the analyte detection zone (31).

19. The lateral flow assay device of claim 1, wherein the one or more mobilizable assay reagents (21) are located on a component of the assay flow path which comprises a first porous material (2), and the one or more immobilized assay reagents (31) are located on the detection member (3) which comprises a second porous material, wherein the first porous material is fluidically connected to the second porous material (3).

20. The lateral flow assay device of claim 1, wherein the one or more mobilizable assay reagents (21) are located within a component of the assay flow path which comprises a first porous material (2), and the one or more immobilized assay reagents (31) are located within the detection member (3) which comprises a second porous material, wherein the first porous material is fluidically connected to the second porous material (3).

* * * * *